United States Patent [19]
Korgel et al.

[11] Patent Number: 5,523,029
[45] Date of Patent: Jun. 4, 1996

[54] METHOD OF ATTACHING A HAPTIC TO AN OPTIC OF AN INTRAOCULAR LENS

[75] Inventors: Scott A. Korgel, Benbrook; Philip M. Bailey, Grapevine, both of Tex.

[73] Assignee: Alcon Laboratories, Inc., Fort Worth, Tex.

[21] Appl. No.: 382,316

[22] Filed: Feb. 1, 1995

[51] Int. Cl.$^6$ .................................................. B29D 11/00
[52] U.S. Cl. ........................... 264/1.37; 264/1.7; 264/482; 623/6
[58] Field of Search ..................... 264/1.36, 1.38, 264/1.37, 1.7, 22, 155, 482; 156/272.9; 219/121.66; 623/6

[56] References Cited

U.S. PATENT DOCUMENTS

| | | |
|---|---|---|
| 3,994,027 | 11/1976 | Jensen et al. |
| 4,104,339 | 8/1978 | Fetz et al. |
| 4,150,471 | 4/1979 | Richards et al. |
| 4,307,043 | 12/1981 | Chase et al. |
| 4,543,673 | 10/1985 | Drake et al. |
| 4,615,702 | 10/1986 | Koziol et al. |
| 4,668,446 | 5/1987 | Kaplan et al. |
| 4,702,865 | 10/1987 | Koziol et al. |
| 4,786,445 | 11/1988 | Portnoy et al. |
| 4,834,749 | 5/1989 | Orlosky. |
| 4,834,751 | 5/1989 | Knight et al. |
| 4,843,209 | 6/1989 | Milligan. |
| 4,863,539 | 9/1989 | Lee et al. |
| 4,894,062 | 1/1990 | Knight et al. |
| 5,074,942 | 12/1991 | Kearns et al. |
| 5,118,452 | 6/1992 | Lindsey et al. |
| 5,133,746 | 7/1992 | Brady et al. |
| 5,147,397 | 9/1992 | Christ et al. |
| 5,171,268 | 12/1992 | Ting et al. |
| 5,201,763 | 4/1993 | Brady et al. |
| 5,250,235 | 10/1993 | Cook et al. |
| 5,252,262 | 10/1993 | Patel. |
| 5,290,892 | 3/1994 | Namdaran et al. |
| 5,306,297 | 4/1994 | Rheinish et al. |
| 5,331,073 | 7/1994 | Weinschenk,III et al. |

FOREIGN PATENT DOCUMENTS

| | | |
|---|---|---|
| 0556040A1 | 2/1993 | European Pat. Off. |
| 63-206240 | 8/1988 | Japan. |

*Primary Examiner*—Mathieu D. Vargot
*Attorney, Agent, or Firm*—Jeffrey S. Schira

[57] ABSTRACT

A method for attaching haptics to an optic of an intraocular lens including the steps of providing the peripheral edge of the optic with at least one hole, inserting an end of the haptic into the hole, aiming a laser which emits radiation within the visible spectrum which is matched to the absorption spectrum of the haptic at a portion of the haptic within the hole and firing the laser so that the radiation passes through the optic essentially without absorption and is absorbed by the haptic, thereby causing the haptic to swell an amount sufficient to mechanically anchor the end of the haptic within the optic.

72 Claims, 7 Drawing Sheets

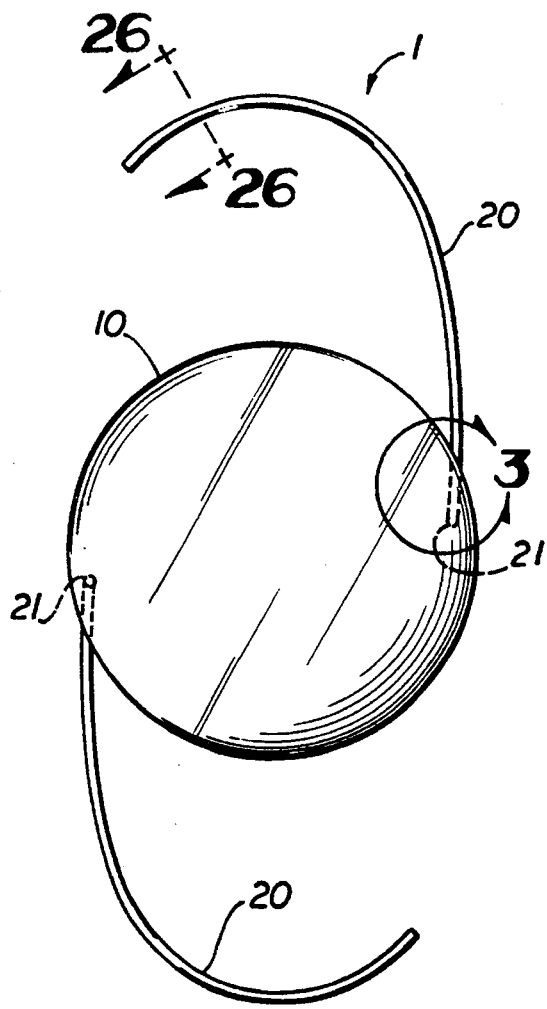
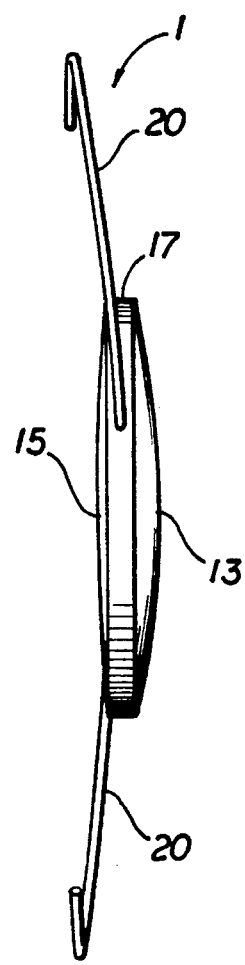
FIG 1    FIG 2
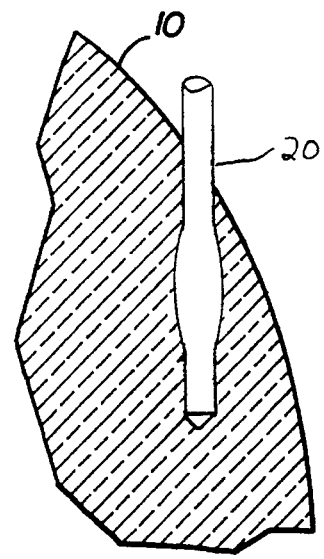
FIG 3

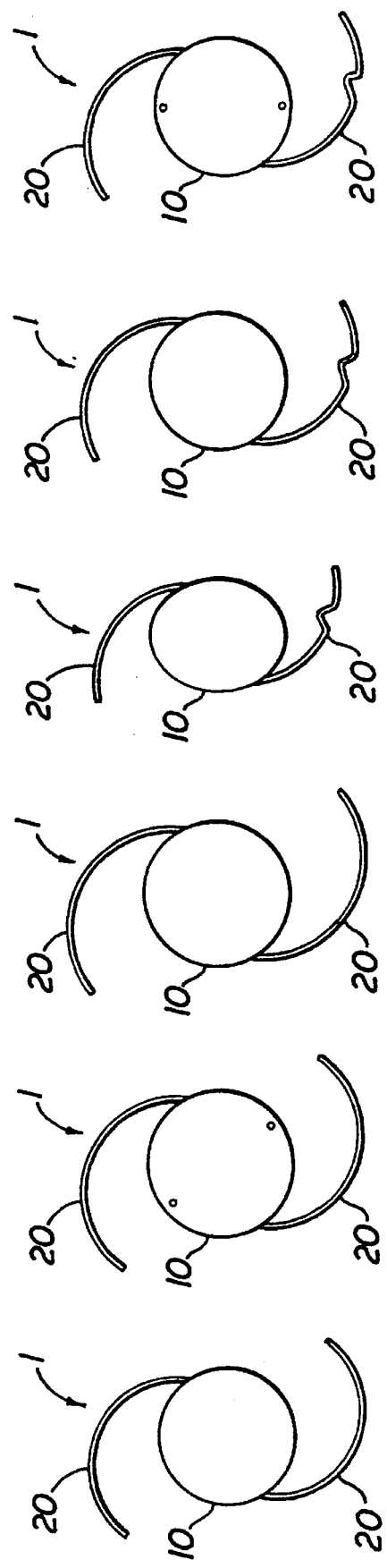
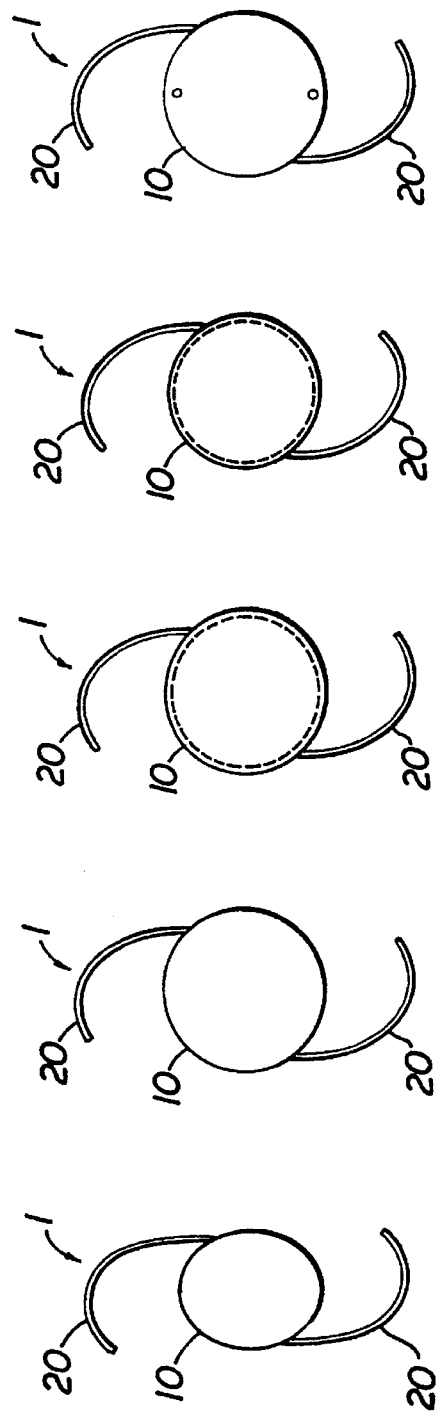

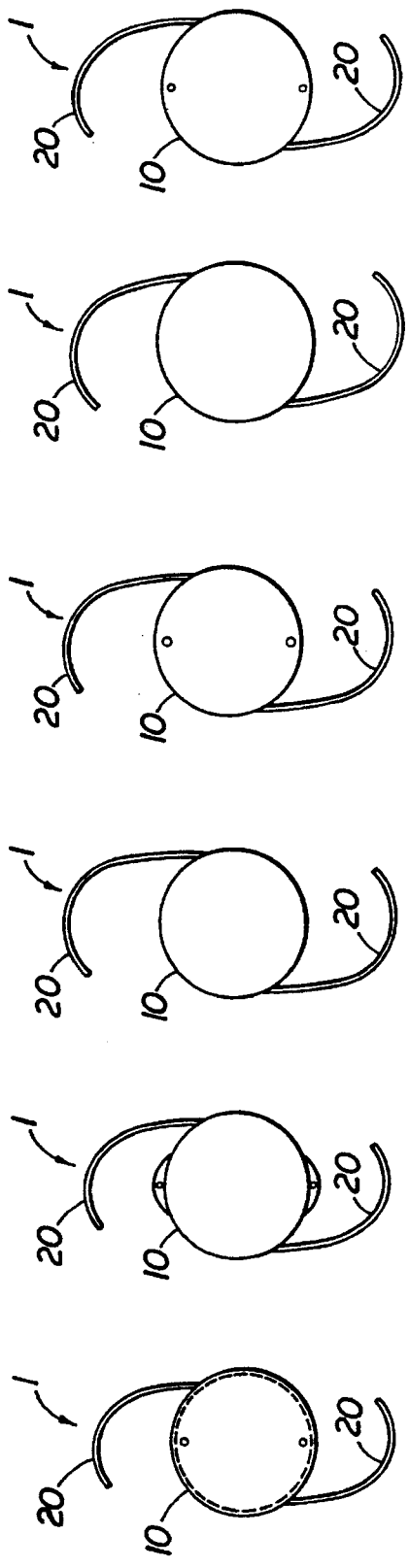
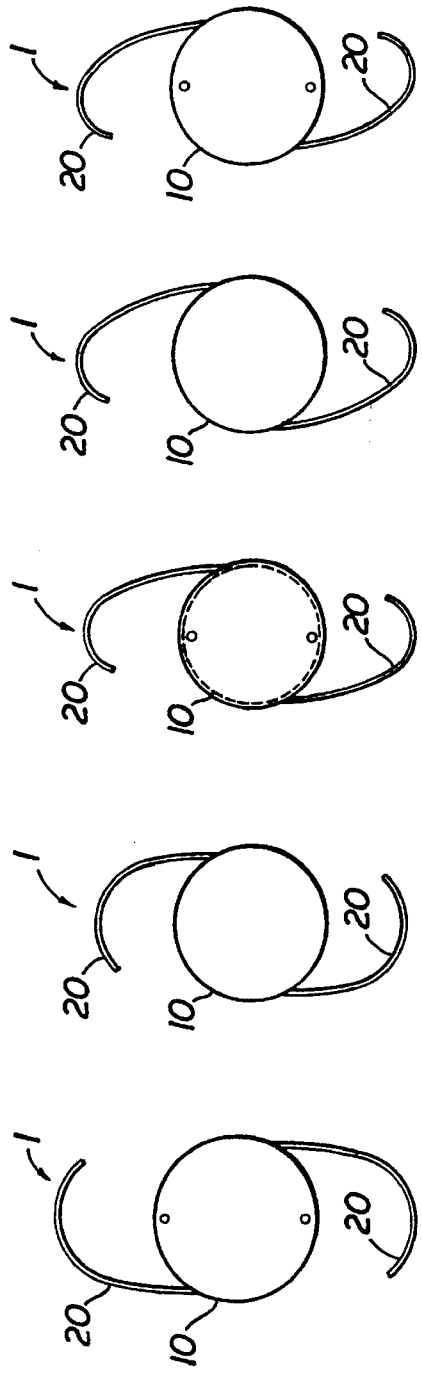
FIG.15 FIG.16 FIG.17 FIG.18 FIG.19 FIG.20
FIG.21 FIG.22 FIG.23 FIG.24 FIG.25

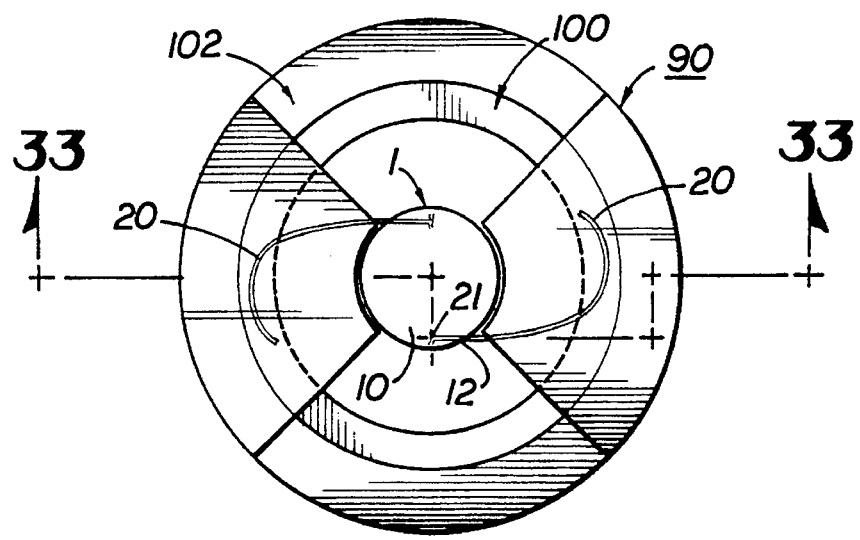
FIG 3.1
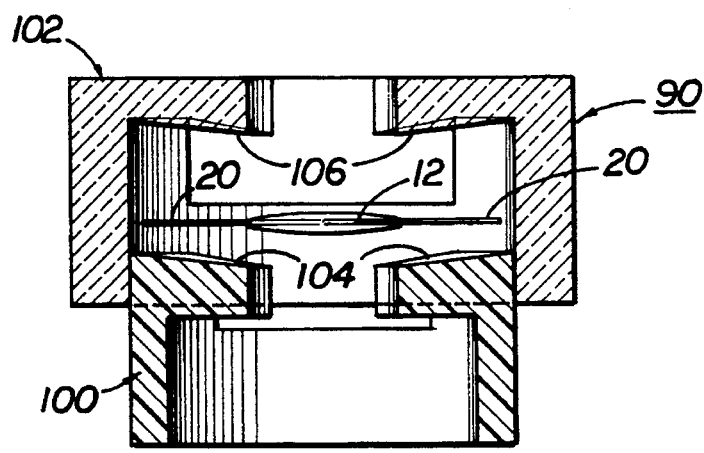
FIG 32
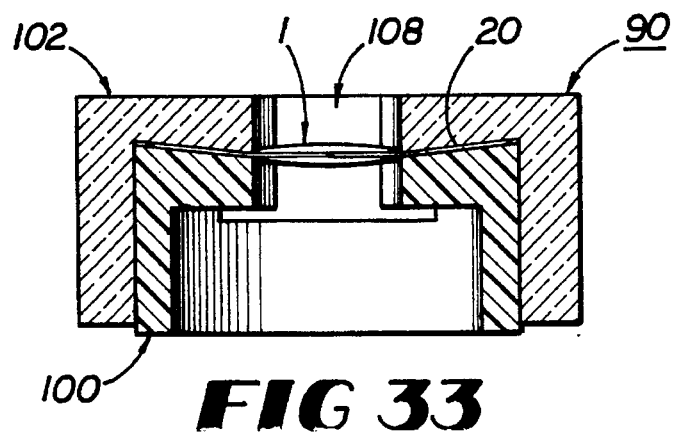
FIG 33

METHOD OF ATTACHING A HAPTIC TO AN OPTIC OF AN INTRAOCULAR LENS

BACKGROUND OF THE INVENTION

The present invention relates to intraocular lenses, particularly to methods for attaching a haptic to an optic using laser welding.

Intraocular lenses have been known since about 1950. They are used to replace the natural lenses of eyes. A typical intraocular lens ("IOL") comprises an artificial lens ("optic") and at least one support member ("haptic") for positioning the IOL within the capsular bag of the eye. The optic may be formed from any of a number of different materials, including polymethylmethacrylate (PMMA), silicones and acrylics, and it may be hard, relatively flexible or even fully deformable so that the IOL can be rolled or folded and inserted through a relatively small incision in the eye. The haptic generally is made of some resilient material, such as polypropylene or flexible copolymers of PMMA. IOLs may be characterized as either "one-piece" or "multi-piece." With one-piece IOLs, the haptic and the optic are formed integrally as a blank and the IOL is then milled or lathed to the desired shape and configuration. The multi-piece IOL are formed either by attaching the haptic to a pre-formed optic or by molding the optic around an end of the haptic.

U.S. Pat. Nos. 4,615,702 and 4,702,865 (Koziol, et al.), U.S. Pat. Nos. 4,834,751 and 4,894,062 (both to Knight, et al.), U.S. Pat. No. 5,171,268 (Ting, et al.), U.S. Pat. Nos. 5,133,746 and 5,201,763 (Brady, et al.), U.S. Pat. No. 5,147,397 (Christ, et al.) and U.S. Pat. No. 5,306,297 (Rheinish, et al.) all describe haptic attachment methods whereby the optic is molded around the end of the haptic. While these methods provide strong haptic-optic interlock, the procedure for molding an optic around the previously joined haptic and anchor member is complex and requires special care to maintain the haptic in place while the optic material is cured, and to remove the cured IOL from the mold without damaging the haptic.

Many methods for attaching a haptic to a pre-formed optic are known, including those involving the use of adhesives. If an adhesive is used to attach a haptic to an optic, the adhesive must be strong, biologically inert and resistant to degradation by bodily fluids. At present, there are few materials that satisfy all these requirements. In addition, there will always be a concern that the adhesive will deteriorate over time, resulting in loose or detached haptics within the eye.

Other more common methods for attaching a haptic to a pre-formed optic involve the use of heat. One such haptic attachment method involves drilling intersecting holes into the periphery of an optic and inserting one end of the haptic into one of the holes. A heated probe is inserted through the other hole, contacting the embedded end of the haptic and causing a portion of it to melt and flow laterally into the second hole. When the embedded haptic end cools and hardens, a mechanical interlock with the optic is formed. A similar method is disclosed in U.S. Pat. No. 4,104,339 (Fetz, et al.), where a haptic hole is made in the peripheral edge of an optic, the haptic end is inserted into the hole and then an inductively heated thin probe is pushed through the posterior face of the optic into contact with the haptic end to form a crimped connection between the haptic and the optic. This is currently the most common method used for attaching haptics to optics. However, this method damages the optic surface where the heated probe is pushed through to the haptic end and thus, compromises optical performance.

Another similar method is disclosed in U.S. Pat. No. 4,307,043 (Chase, et al.), where a hole having threaded recesses is made through a portion of the optic (the hole being essentially parallel to the plane of the optic) and one end of a haptic is inserted through the hole so that it projects beyond the optic. Heat is then applied to the haptic end projecting beyond the optic to melt a portion of it, which fills the threaded portions of the hole. When the haptic material hardens, a mechanical interlock with the optic is formed. This heat attachment technique is disadvantageous because skilled technicians and precise equipment alignment are required.

U.S. Pat. No. 4,786,445 (Portnoy, et al.) discloses another haptic attachment method which involves making a cavity having a shoulder in the periphery of an optic. The haptic end is inserted into the cavity and laser energy of a near infrared wavelength is transmitted through the optic to the haptic, causing the haptic end to melt and flow into the shoulder of the cavity. When the end hardens, a mechanical interlock between the haptic and the optic is formed. Although this method avoids some of the problems of the prior-mentioned methods, there are other disadvantages. Because the haptic end is melted to form a shoulder within the cavity of the optic, there is a likelihood of variation in haptic length, both between individual IOL and between individual haptics attached to the same IOL.

U.S. Pat. No. 4,843,209 (Milligan) discloses a method of attaching a haptic to an optic using laser energy. However, the method disclosed uses a high-powered neodymium:yttrium-aluminum-garnet (Nd:YAG) laser that emits radiation in the non-visible spectrum, necessitating the use of a Helium-Neon (HeNe) aiming laser, and resulting in exacting Nd:YAG/HeNe laser alignment requirements. Furthermore, the method disclosed in this patent does not rely on a differential in laser energy absorption between the haptic and the optic to prevent optic damage (both the optic and the haptic being disclosed as comprising PMMA) and, instead, the disclosed method must carefully balance the amount of laser energy used with the time of exposure to insure that the optic is not damaged. The haptic absorbs the laser energy more readily than the optic because the optic has a smooth, flat surface while both the haptic and the hole in the optic contain a series of interlocking ridges that diffusion and deflect the radiation within the haptic This absorption method is inefficient, requiring the use of a relatively high laser power level (on the order of 50 watts) and is unnecessarily complex and expensive because of the difficulty in forming the ridges in the hole and on the haptic.

U.S. Pat. No. 5,118,452 (Lindsey, et al.) discloses a laser method of attaching a haptic to a soft optic; however, the method disclosed in this patent requires the use of a separate, intersecting anchor strand fused to the haptic end to hold the haptic within the optic.

U.S. Pat. No. 5,252,262 (Patel) discloses a method of attaching a haptic within an optic using visible laser light. The method disclosed in this patent requires a fusion bond between the haptic and the optic, thereby requiring that the optic and the haptic be made from the same or similar (thermoplastic) materials.

Accordingly, a need has continued to exist for a simple, reliable method of attaching a thermoplastic haptic to a soft optic of an intraocular lens without damaging the optic or otherwise distorting the optical properties of the optic.

BRIEF SUMMARY OF THE INVENTION

The present invention improves upon prior art methods of attaching a haptic to an optic by providing a method for using laser energy to attach a haptic to an optic without damaging the optic while producing a strong mechanical interlock between the haptic and the optic. This is accomplished by forming a single, smooth mounting hole in the peripheral edge of a relatively soft optic in the plane normal to the optical axis of the optic, inserting the smooth end of a colored, thermoplastic haptic into the hole and transmitting laser energy within the visible spectrum through the optic to the portion of the haptic within the optic, whereby the haptic is heated sufficiently to cause the haptic to swell slightly, forming a solid, mechanical interlock between the haptic and the optic. The use of a colored haptic and a laser transmitting energy in the visible spectrum allows the laser energy to be transmitted through the optic without damaging the optic, while at the same time, increasing the absorption of the laser energy by the haptic. Therefore, equipment alignment tolerances are more generous. The use of a visible laser energy source also is less hazardous than other invisible forms of laser energy because the laser beam is easily seen and thus more readily avoided.

Accordingly, one objective of the present invention is to provide a method of attaching an intraocular lens haptic to an optic that does not damage the optic.

Another objective of the present invention is to provide a method of laser welding an intraocular lens haptic to an optic that does not require precise alignment of the welding laser.

Another objective of the present invention is to provide a method of attaching an intraocular lens haptic to an optic that is simple and inexpensive.

Still another objective of the present invention is to provide a method of attaching an intraocular lens haptic to an optic using a visible laser.

A further objective of the present invention is to provide a method of attaching an intraocular lens haptic to an optic that requires only a single haptic mounting hole in the optic.

Another objective of the present invention is to provide a method of attaching an intraocular lens haptic having a colored core to an optic.

Yet another objective of the present invention is to provide a method of attaching a thermoplastic optic to a soft optic.

These and other objectives and advantages of the present invention will become apparent from the detailed description, drawings and claims that follow.

BRIEF DESCRIPTION OF THE DRAWING

FIG. 1 is a posterior plan view of a typical IOL made in accordance with the methods of the present invention.

FIG. 2 is an elevation view of the IOL illustrated in FIG. 1.

FIG. 3 is a fragmentary cross-section of the IOL illustrated in FIG. 1 taken at circle 3 and showing the swelled end of the haptic.

FIGS. 4–25 are anterior plan views, similar to FIG. 1, of alternative embodiments of IOL made in accordance with the methods of the present invention.

FIG. 31 is a top plan view of the fixture illustrated in FIG. 30.

FIGS. 32 and 33 is a cross sectional view of the fixture illustrated in FIG. 30 taken along line 33—33 in FIG. 31.

DETAILED DESCRIPTION OF THE INVENTION

Figure 26:
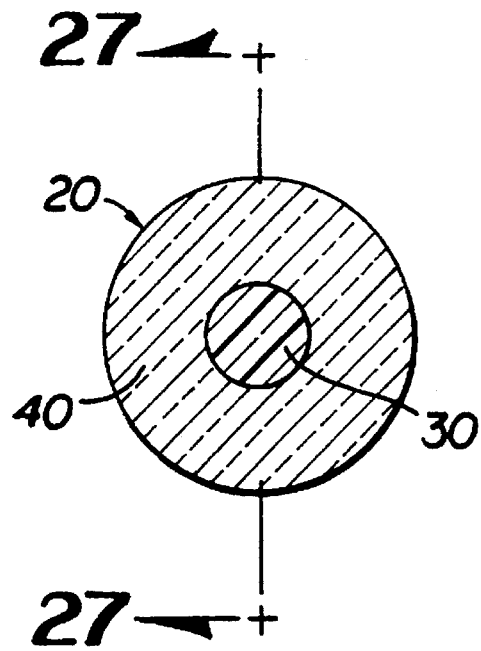
FIG. 26 is a cross-section of a first embodiment of the haptic made in accordance with the methods of the present invention taken at line 26—26 in FIG. 1.

As can be seen in FIGS. 1 and 2, IOL i includes an optic 10 and at least one haptic 20. As illustrated in FIGS. 4–25, haptics 20 may be configured in any of a number of ways and the optic 10 may have any of a number of closed-curve shapes, such as a circle, an oval or an ellipse. Although several suitable optics 10 and haptics 20 configurations are illustrated in FIGS. 1, 2 and 4–25, other suitable shapes, sizes and configurations may also be used.

Optic 10 has anterior face 13, posterior face 15 and peripheral edge 17. Optic 10 may be made of any suitable, biocompatible material, such as PMMA, polycarbonate, hydrogel, silicone or acrylic materials such as those described in U.S. Pat. No. 5,290,892 (Namdaran) and U.S. Pat. No. 5,331,073 (Weinschenk, III, et al.), the entire contents of which are incorporated herein by reference. Optic 10 is preferably between 4.50 millimeters (mm) and 7.00 mm across.

Figure 27:
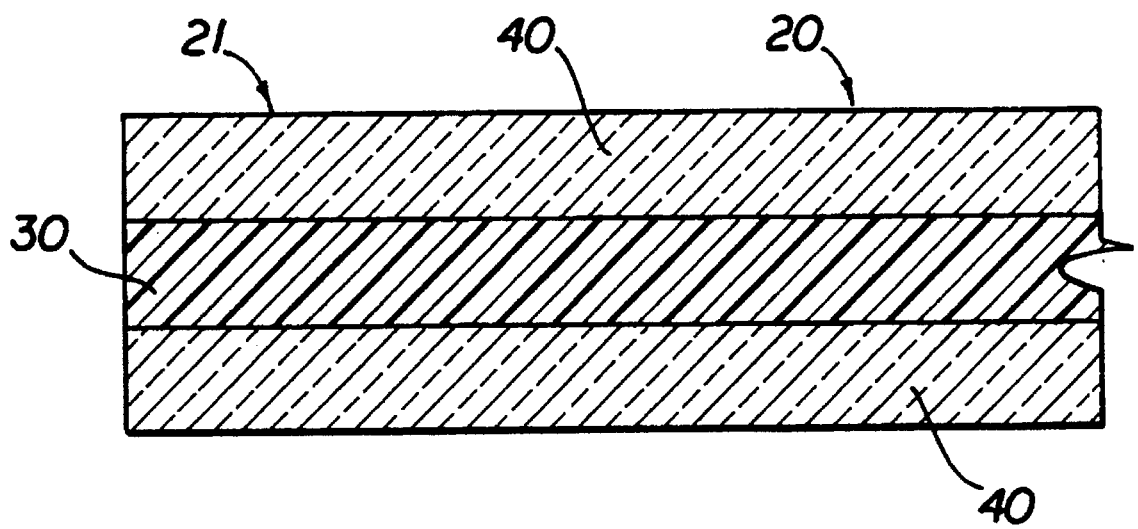
FIG. 27 is a longitudinal cross-section of an end portion of the first embodiment of the haptic of the present invention taken perpendicularly to the cross-section illustrated in FIG. 26 at line 27—27.
Figure 28:
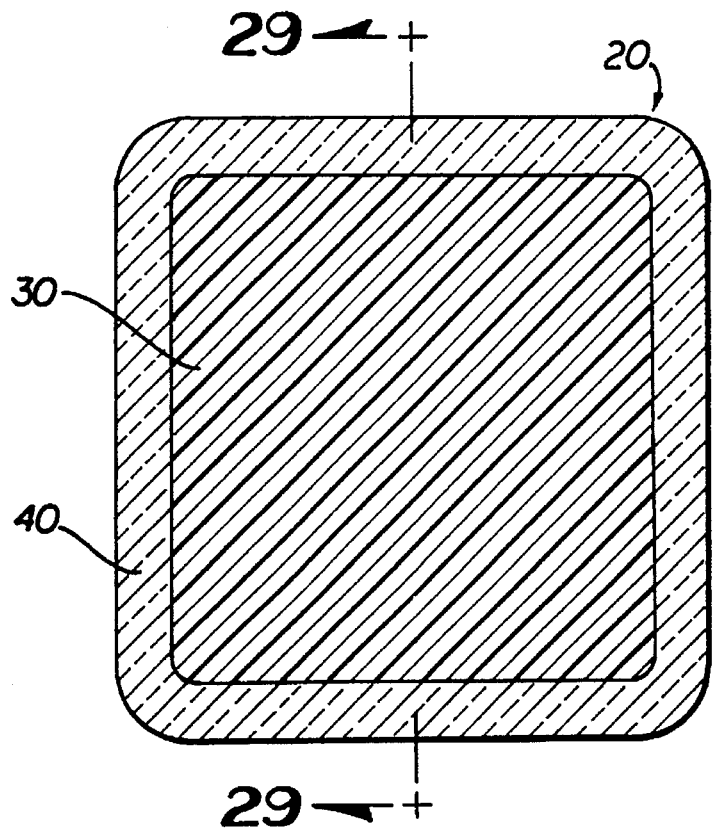
FIG. 28 is a cross-section of a second embodiment of the haptic made in accordance with the methods of the present invention similar to FIG. 26.
Figure 29:
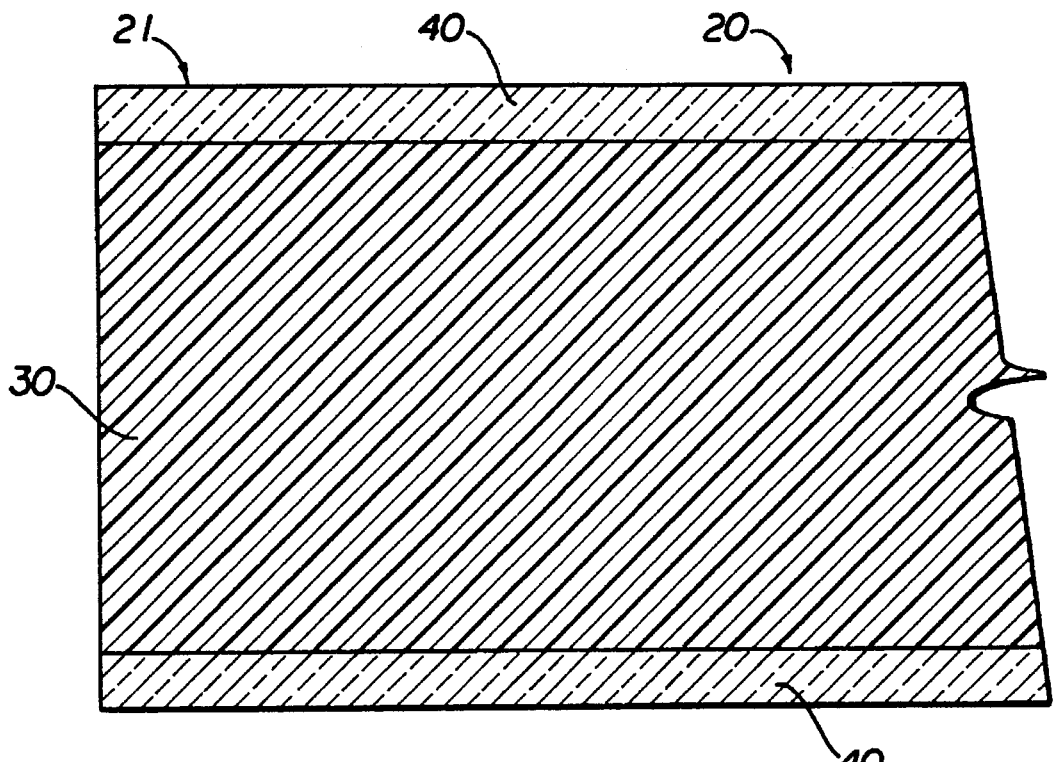
FIG. 29 is a longitudinal cross-section of an end portion of the second embodiment of the haptic of the present invention taken perpendicularly to the cross-section illustrated in FIG. 28 at line 29—29.
Figure 30:
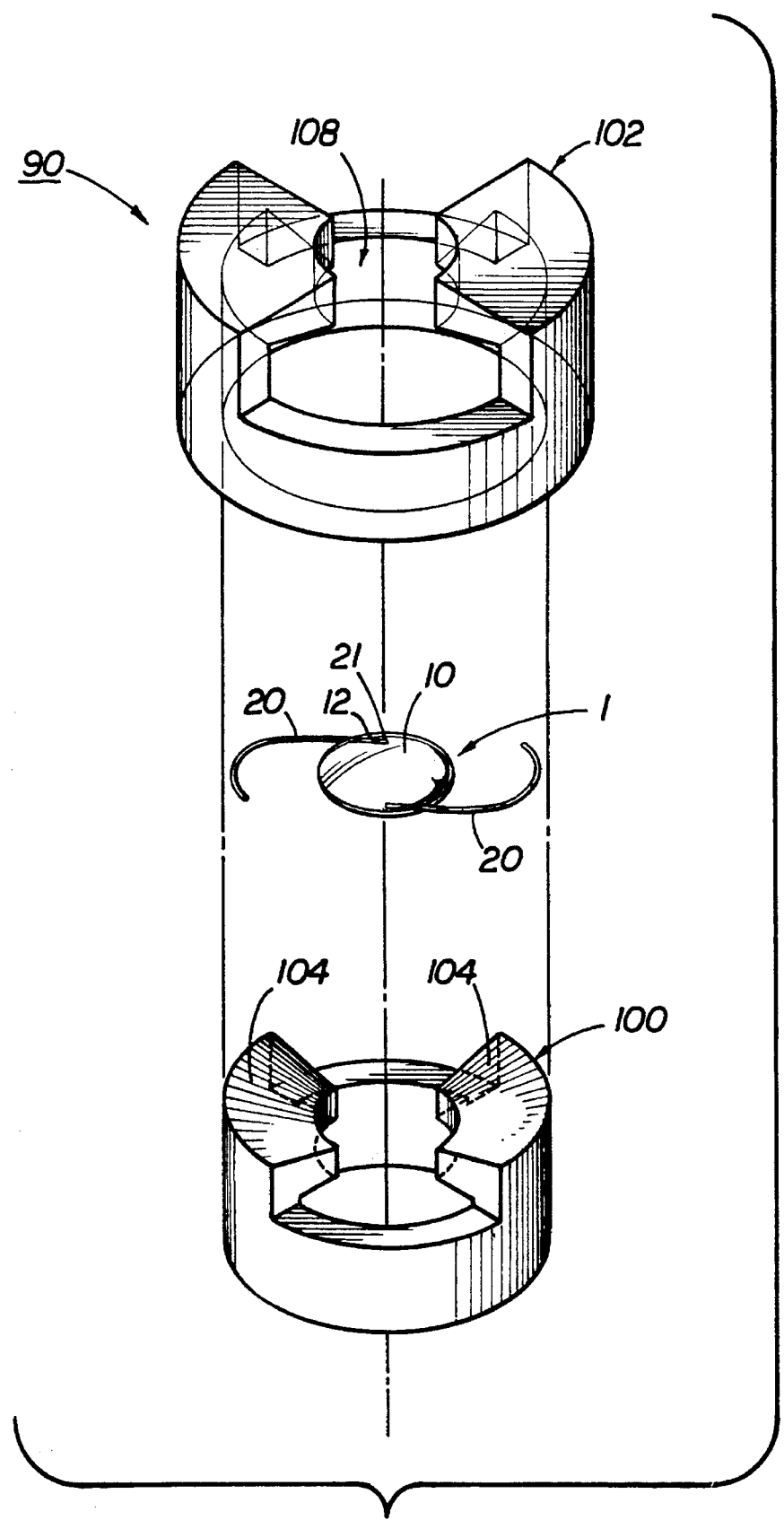
FIG. 30 is an expanded perspective view of a fixture that may be used for practicing the present invention.

Haptics 20 are formed separately from optic 10 by injection molding, extrusion, thermal-drawing or any other suitable method. Haptic 20 may be of any suitable cross-sectional shape, such as round, as illustrated in FIGS. 26 and 27, rectangular with rounded corners, as illustrated in FIGS. 28 and 29, oval, elliptical, hexagonal or other geometric shape and is preferably smooth and at least end portion 21 of haptic 20 to be attached to optic 10 must be a colored material, such as blue, green or violet. Alternatively, as can be seen in FIGS. 26–29, haptic 20 may have a colored core 30 surrounded by a clear sheath 40. The use of core 30 surrounded by sheath 40 helps to minimize any possible leaching of the pigment used to color core 30 from haptic 20. Round haptic 20 (illustrated in FIGS. 26 and 27) generally has a diameter of approximately between 0.105 and 0.175 mm, with between approximately 0.127 and 0.152 mm being preferred, and the diameter of core 30 may be anywhere within the same range as the diameter of haptic 20. Rectangular haptic 20 (illustrated in FIGS. 28 and 29) preferably has a width of between approximately 0.11 and 0.14 mm and a height of approximately between 0.14 and 0.16 mm, for example, 0.127 mm wide by 0.152 mm high with the dimensions of core 30 approximating the overall dimensions of haptic 20. Haptic 20 may be made of any of a number of thermoplastics such as PMMA, polypropylene, polycarbonate, polyimides, polyvinylidene difluoride or copolymers of esters of acrylic acid and methacrylic acid. If the material used to form haptic 20 is naturally non-colored, the material must either include a pigment, a dye or be combined with a colored material. One suitable haptic material is available from Rohm and Haas under the tradename VS100 which, upon adding copper phthalocyanine, gives the raw material necessary for forming colored haptics 20. Other preferred haptic materials include PMMA with a copper phthalocyanine-doped core 30, blue polypropylene or a violet or green colored thermoplastic such as PMMA.

The laser (not shown) used to weld haptic 20 to optic 10 must emit radiation in the visible spectrum, approximately between 400 and 700 nanometers (nm) and is preferably a continuous wave (CW) laser. Visible wavelength laser energy will be at least partially absorbed by the colored haptic material, regardless of the specific wavelength of energy used or the color of haptic 20; however, it is preferable that the laser energy spectrum used be matched with the absorption spectrum of the material used to form haptic 20 or core 30. For example, if haptic 20 or core 30 is blue, it is generally preferred that the visible laser energy spectrum have some wavelengths in the deep blue, green or red portions of the visible spectrum absorbed by haptic 20 or core 30. Such a spectrum is emitted from Krypton, Argon, Helium-Neon or tunable dye lasers for a copper phthalocyanine-doped PMMA haptic 20.

Hole 12 in optic 10 may be made in any suitable manner and be formed either after optic 10 has been formed, such as by drilling, or optic 10 may be formed with hole 12 pre-formed, such as by the methods disclosed in U.S. Pat. Nos. 5,185,107 and 5,104,590 (Blake), the entire contents of which being incorporated herein by reference. Hole 12 is preferably smooth and less than 1 mm deep and should be only slightly larger in diameter than the maximum cross-sectional dimension of haptic 20 so that haptic 20 fits snugly within hole 12.

To attach haptic 20 to optic 10, end portion 21 of haptic 20 is inserted fully into hole 12. The laser (not shown) is aimed at end portion 21 of haptic 20 within hole 12 in optic 10 and fired. The laser energy is fully transmitted through transparent optic 10 without damaging optic 10 while the pigment or dye in haptic 20 or in core 30 absorbs the laser energy and heats to a temperature sufficient to cause end portion 21 to swell and interlock end portion 21 within hole 12 as shown in FIG. 3. The laser energy level needed to fuse haptic 20 and optic 10 will vary with the materials used for optic 10, haptic 20 and core 30, but generally will be less than 5 watts. By way of example, when an Argon (CW) or Krypton (CW) laser is used and haptic 20 is made from the colored VS100 material (PMMA with a copper phthalocyanine-doped core), the laser output required to lock haptic 20 within optic 10 is approximately between 0.10 and 1.0 watts with a laser exposure time of approximately between 1 and 3 seconds when a laser spot size of approximately 100 microns is used. While heating of the haptic may cause air bubbles to form in the swelled region of the haptic, air bubble formation can be minimized by reducing the power of the laser or by moving the laser during the attachment procedure so that the laser spot does not stay fixed at a specific point on the haptic.

The method of the present invention may also be used in anneal haptics 20 at an angle, generally between 0° and 10°. Angling haptics 20 vaults IOL 1 away from the iris when implanted. The memory properties of the thermoplastic materials used to make haptics 20 cause haptics 20, when warmed, to be easily formed and to retain any new shape. Prior art methods of annealing IOLs generally included placing the IOLs in a fixture and warming the IOL-retaining fixture in an oven or warm liquid bath. Such a process is more fully described in U.S. Pat. No. 4,543,673 (Drake, et al.) the entire contents of which is incorporated herein by reference. The present method uses the warming of the haptic by the attachment laser to anneal or set haptics 20 at any desired angle, without drilling hole 12 at an angle.

As can be seen in FIGS. 30–33, annealing fixture 90 includes rest plate 100 that telescopes into cap plate 102 so that IOL 1 is sandwiched between rest plate 100 and cap plate 102 with haptics 20 held between angled surfaces 104 in rest plate 100 and angled surfaces 106 in cap plate 102. Angled surfaces 104 and 106 may be set at any desired angle, and plates 100 and 102 may be made from any suitable material such as stainless steel, polytetrafluoroethylene (TEFLON®, polysulfone or DELRIN®. Bore 108 in cap plate 102 allows the portion of haptics 20 within optic 10 to remain exposed, as best seen in FIG. 31. To anneal haptics 20, the haptic attachment method described above is performed with IOL 1 placed in fixture 90. During laser irradiation, a small amount of the heat generated within end portion 21 is conducted throughout haptic 20, thereby annealing or setting haptic 20 without the need separately to warm fixture 90 containing IOL 1 in an oven or liquid bath.

This description is given for purposes of illustration and explanation. It will be obvious to those skilled in the relevant art that modifications may be made to the invention as described herein without departing from its scope or spirit.

We claim:
1. A method for attaching at least one haptic to an optic of an intraocular lens, comprising the steps of:
   a. providing a peripheral edge of the optic with at least one hole;
   b. inserting an end of the haptic into the hole;
   c. aiming at a portion of the haptic within the hole a laser having a power level of less than 1 watt and emitting radiation within a visible spectrum that is matched to the absorption spectrum of the haptic; and
   d. firing the laser so that the radiation passes through the optic essentially without absorption and is absorbed by the portion of the haptic within the hole, thereby causing the portion of the haptic within the hole to swell an amount sufficient to anchor mechanically the end of the haptic within the optic.

2. The method of claim 1 wherein the haptic comprises a violet-colored material.

3. The method of claim 1 wherein the haptic comprises a green-colored material.

4. The method of claim 1 wherein haptic comprises a blue-colored material.

5. The method of claim 4 wherein the blue-colored material comprises polymethylmethacrylate with a copper phthalocyanine-doped core.

6. The method of claim 1 wherein the optic comprises silicone.

7. The method of claim 1 wherein the optic comprises a thermoplastic.

8. The method of claim 1 wherein the optic comprises an acrylic.

9. The method of claim 1 wherein the haptic comprises thermoplastic.

10. The method of claim 9 wherein the thermoplastic comprises copolymers of esters of acrylic acid and methacrylic acid.

11. The method of claim 9 wherein the thermoplastic comprises polymethylmethacrylate.

12. The method of claim 9 wherein the thermoplastic comprises a polyamide.

13. The method of claim 9 wherein the thermoplastic comprises polyvinylidene difluoride.

14. The method of claim 9 wherein the thermoplastic comprises polypropylene.

15. The method of claim 1 wherein the visible spectrum comprises a wavelength from about 400 nanometers to about 700 nanometers.

16. The method of claim 1 wherein the laser comprises an Argon laser.

17. The method of claim 1 wherein the laser comprises a tunable dye laser.

18. The method of claim 1 wherein the laser comprises a Krypton laser.

19. The method of claim 1 wherein the laser comprises a Helium-Neon laser.

20. The method of claim 1 wherein the hole is drilled in the peripheral edge of the optic.

21. The method of claim 1 wherein a shape of the optic is a closed curve.

22. A method for attaching at least one thermoplastic haptic to an acrylic optic of an intraocular lens, comprising the steps of:
   a. forming at least one hole in a peripheral edge of the optic;
   b. inserting an end of the haptic into the hole;
   c. aiming at a portion of the haptic within the hole a laser having a power level of less than 1 watt and emitting radiation within a wavelength range of approximately between 400 nanometers and 700 nanometers that is matched to the absorption spectrum of the haptic; and
   d. firing the laser so that the radiation passes through the optic essentially without absorption and is absorbed by the portion of the haptic within the hole, thereby causing the portion of the haptic within the hole to swell an amount sufficient to anchor mechanically the end of the haptic within the optic.

23. The method of claim 22 wherein the thermoplastic comprises copolymers of esters of acrylic acid and methacrylic acid.

24. The method of claim 22 wherein the thermoplastic comprises polymethylmethacrylate.

25. The method of claim 24 wherein the haptic further comprises a copper phthalocyanine-doped core.

26. The method of claim 22 wherein the thermoplastic comprises a polyamide.

27. The method of claim 22 wherein the thermoplastic comprises polyvinylidene difluoride.

28. The method of claim 22 wherein the thermoplastic comprises polypropylene.

29. The method of claim 22 wherein the laser comprises an Argon laser.

30. The method of claim 22 wherein the laser comprises a tunable dye laser.

31. The method of claim 22 wherein the laser comprises a Krypton laser.

32. The method of claim 22 wherein the laser comprises a Helium-Neon laser.

33. The method of claim 22 wherein a shape of the optic is a closed curve.

34. A method for attaching at least one haptic to an optic of an intraocular lens, comprising the steps of:
   a. forming the haptic from polymethylmethacrylate;
   b. forming at least one hole in a peripheral edge of the optic;
   c. inserting an end of the haptic into the hole;
   d. aiming at a portion of the haptic within the hole an Argon laser having a power level of less than 1 watt and emitting radiation within a visible spectrum that is matched to the absorption spectrum of the haptic; and
   e. firing the laser so that the radiation passes through the optic essentially without absorption and is absorbed by the haptic, thereby causing portion of the haptic within the hole to swell an amount sufficient to anchor mechanically the end of the haptic within the optic.

35. The method of claim 34 wherein the optic comprises silicone.

36. The method of claim 34 wherein the optic comprises an acrylic.

37. The method of claim 34 wherein the optic comprises PMMA.

38. The method of claim 34 wherein a shape of the optic is a closed curve.

39. A method for attaching at least one haptic to an optic of an intraocular lens, comprising the steps of:
   a. forming the haptic from polymethylmethacrylate;
   b. forming at least one hole in a peripheral edge of the optic;
   c. inserting an end of the haptic into the hole;
   d. aiming at a portion of the haptic within the hole a Krypton laser having a power level of less than 1 watt and emitting radiation within a visible spectrum that is matched to the absorption spectrum of the haptic; and
   e. firing the laser so that the radiation passes through the optic essentially without absorption and is absorbed by the haptic, thereby causing portion of the haptic within the hole to swell an amount sufficient to anchor mechanically the end of the haptic within the optic.

40. The method of claim 39 wherein the optic comprises silicone.

41. The method of claim 39 wherein the optic comprises an acrylic.

42. The method of claim 39 wherein the optic comprises PMMA.

43. The method of claim 39 wherein a shape of the optic is a closed curve.

44. A method for attaching at least one haptic to an optic of an intraocular lens, comprising the steps of:
   a. forming the haptic from polymethylmethacrylate;
   b. forming at least one hole in a peripheral edge of the optic;
   c. inserting an end of the haptic into the hole;
   d. aiming at a portion of the haptic within the hole a tunable dye laser having a power level of less than 1 watt and emitting radiation within a visible spectrum that is matched to the absorption spectrum of the haptic; and
   e. firing the laser so that the radiation passes through the optic essentially without absorption and is absorbed by the haptic, thereby causing portion of the haptic within the hole to swell an amount sufficient to anchor mechanically the end of the haptic within the optic.

45. The method of claim 44 wherein the optic comprises silicone.

46. The method of claim 44 wherein the optic comprises an acrylic.

47. The method of claim 44 wherein the optic comprises PMMA.

48. The method of claim 44 wherein a shape of the optic is a closed curve.

49. A method for attaching at least one haptic to an optic of an intraocular lens, comprising the steps of:
   a. forming the haptic from polymethylmethacrylate;
   b. forming at least one hole in a peripheral edge of the optic;
   c. inserting an end of the haptic into the hole;
   d. aiming at a portion of the haptic within the hole a Helium-Neon laser having a power level of less than 1 watt and emitting radiation within a visible spectrum that is matched to the absorption spectrum of the haptic; and e. firing the laser so that the radiation passes through the optic essentially without absorption and is absorbed by the haptic, thereby causing portion of the haptic within the hole to swell an amount sufficient to anchor mechanically the end of the haptic within the optic.

50. The method of claim 49 wherein the optic comprises silicone.

51. The method of claim 49 wherein the optic comprises an acrylic.

52. The method of claim 49 wherein the optic comprises PMMA.

53. The method of claim 49 wherein a shape of the optic is a closed curve.

54. A method for attaching at least one haptic to an optic of an intraocular lens, comprising the steps of:
   a. forming the haptic from a thermoplastic;
   b. forming at least one hole in a peripheral edge of the optic;
   c. inserting an end of the haptic into the hole;
   d. holding the haptic in a fixture at an angle relative to the plane of the optic;
   e. aiming at a portion of the haptic within the hole a laser having a power level of less than 1 watt and emitting radiation within a visible spectrum that is matched to the absorption spectrum of the haptic; and
   f. firing the laser so that the radiation passes through the optic essentially without absorption and is absorbed by the haptic, thereby causing the portion of the haptic within the hole to anchor mechanically within the optic and warming the haptic an amount sufficient to set the haptic at the angle.

55. The method of claim 54 wherein the optic comprises silicone.

56. The method of claim 54 wherein the optic comprises an acrylic.

57. The method of claim 54 wherein the optic comprises PMMA.

58. The method of claim 54 wherein a shape of the optic is a closed curve.

59. The method of claim 54 wherein the haptic comprises a violet-colored material.

60. The method of claim 54 wherein the haptic comprises a green-colored material.

61. The method of claim 54 wherein haptic comprises a blue-colored material.

62. The method of claim 61 wherein the blue-colored material comprises polymethylmethacrylate with a copper phthalocyanine-doped core.

63. The method of claim 54 wherein the thermoplastic comprises copolymers of esters of acrylic acid and methacrylic acid.

64. The method of claim 63 wherein the thermoplastic comprises polymethylmethacrylate.

65. The method of claim 63 wherein the thermoplastic comprises a polyamide.

66. The method of claim 63 wherein the thermoplastic comprises polyvinylidene difluoride.

67. The method of claim 63 wherein the thermoplastic comprises polypropylene.

68. The method of claim 54 wherein the visible spectrum comprises a wavelength from about 400 nanometers to about 700 nanometers.

69. The method of claim 54 wherein the laser comprises an Argon laser.

70. The method of claim 54 wherein the laser comprises a tunable dye laser.

71. The method of claim 54 wherein the laser comprises a Krypton laser.

72. The method of claim 54 wherein the laser comprises a Helium-Neon laser.

* * * * *